United States Patent [19]

Romano et al.

[11] 4,045,464

[45] Aug. 30, 1977

[54] PROCESS FOR THE PREPARATION OF AROMATIC CARBONATES

[75] Inventors: Ugo Romano, Milan; Renato Tesei, San Donato Milanese, both of Italy

[73] Assignee: Anic, S.p.A., Palermo, Italy

[21] Appl. No.: 636,604

[22] Filed: Dec. 1, 1975

[30] Foreign Application Priority Data

Nov. 25, 1974 Italy ................................. 29773/74

[51] Int. Cl.$^2$ ............................................. C07C 68/06
[52] U.S. Cl. ................................................... 260/463
[58] Field of Search ........................................ 260/463

[56] References Cited

U.S. PATENT DOCUMENTS 3,517,029  6/1970  Johnson ............................. 260/463
3,655,626  4/1972  Kolobielski ........................ 260/463

FOREIGN PATENT DOCUMENTS 1,217,349  5/1967  United Kingdom ................. 260/463

*Primary Examiner*—Delbert R. Phillips
*Attorney, Agent, or Firm*—Ralph M. Watson

[57] ABSTRACT

The invention relates to a process for preparing diaryl carbonates starting from phenyl alkyl carbonates, the reaction being carried out in the presence of suitable catalysts capable of affording greater yields and selectivity; the catalyst system is selected amongst the Lewis acids or the compounds of transition metals.

4 Claims, No Drawings

PROCESS FOR THE PREPARATION OF AROMATIC CARBONATES

The present invention refers to a process for the preparation of aromatic carbonates of formula

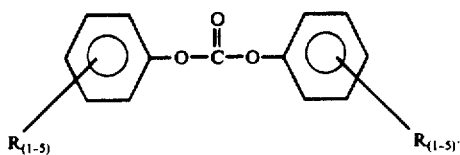

I where R is a substituent chosen among the alkyl, alkoxy, aryl, aryloxy or $NO_2$ groups, or Rydrogen, starting from compounds of formula

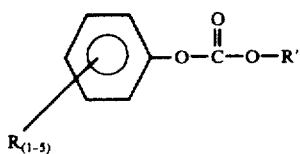

II where $R^1$ is a non-tertiary alkyl group.

It is known that the di-aryl-carbonates are prepared starting from the respective phenols with phosgene by means of a complex technology which entails considerable risks and that implies the formation as by-product of hydrochloric acid. The aromatic carbonates have a considerable industrial interest as they are used as intermediates in the production of aromatic polycarbonates and in the synthesis of some isocyanates.

It has now been found, and this is the subject of the present invention, that it is possible to obtain with high yields and selectivity diaryl carbonates by reacting phenyl alkyl carbonates in presence of suitable catalysts. From the reaction, besides diaryl carbonates dyalkyl carbonates are obtained in equimolecular quantities.

The reaction is carried out in liquid phase with or without solvents at temperatures between 25° and 350° C and preferably between 80° and 250° C at pressures between 0.1 and 100 absolute atmospheres and preferably between 1 and 25 absolute atmospheres.

Efficient catalysts are those with formula Al $X_3$, Ti $X_3$, $UX_4$, Ti $X_4$, VO $X_3$, $VX_5$, Zn $X_2$, Fe $X_3$, Sn $X_4$ where X is a halogen, acetoxy, alkoxy, aryloxy, and generally Lewis' acids or compounds of transition metals which generate them.

The Lewis' acids may be used by themselves or blended or adducts of the same with organic molecules may be used.

Some illustrative but not limitative examples are reported hereunder.

EXAMPLE 1

For 4 hours at 180° C one mole of phenyl- ethyl carbonate and 0.023 moles of titatium tetraphenate were reacted.

A 40 % conversion was obtained of phenyl ethyl carbonate with selectivity to diphenyl carbonate and di-ethyl carbonate higher than 95 %, having been formed even small quantities of phenyl-ethyl ether.

EXAMPLE 2

For 4 hours at 180° C, 60 gr of phenyl-methyl carbonate were reacted and 1.5 gr of titanium tetramethylate in presence in 50 cc of normal hexane by continuously distilling the azeotrope dimethyl carbonate-hexane at a reflux ratio 20/1.

A 63 % conversion of phenyl-methyl carbonate was obtained, with selectivity higher than 95 % to diphenyl carbonate and dimethyl carbonate, small quantities of anisole being present.

EXAMPLE 3

For 4 hours at 180° C, 60 gr of phenyl-ethyl carbonate were reacted, 3.5 gr of titanium tetraphenate and 60 cc of ethyl cyclohexane by continuously distilling the diethyl carbonate-hydrocarbon azeotrope at a 20/1 reflux ratio.

A 70 % conversion of phenyl-ethylcarbonate was obtained with a selectivity higher than 95 % to diphenyl carbonate and diethyl carbonate with small quantities of phenyl-ethyl ether.

We claim:

1. A process for the preparation of aromatic carbonates of the formula:

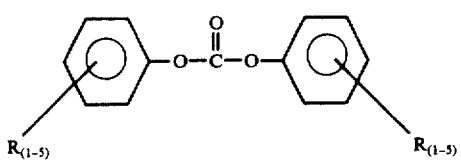

I wherein R is selected from among the alkyl, alkoxy, aryl, aryloxy, $NO_2$ groups, and hydrogen, comprising contacting the compound of the formula:

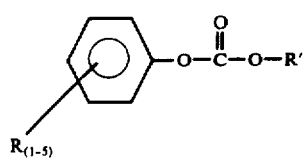

II wherein R has the same meaning as in Formula I and wherein R' is a non tertiary alkyl group, with a catalyst system comprised of titanium tetraphenate or titanium tetramethylate, at a temperature of 25° - 350° C and at a pressure of from 0.1 - 100 atmospheres absolute.

2. A process as claimed in claim 1 wherein said compound of Formula II is contacted with said catalyst at a temperature of from 80° - 250° C and at a pressure of from 1 to 25 atmospheres absolute.

3. A process as claimed in claim 1 wherein R is hydrogen and wherein R' is selected from among methyl and ethyl.

4. A process as claimed in claim 2 wherein R is hydrogen and wherein R' is selected from among methyl and ethyl.

* * * * *